(12) United States Patent
Brown

(10) Patent No.: US 10,206,794 B2
(45) Date of Patent: Feb. 19, 2019

(54) PROSTHETIC ATTACHMENT LOCK

(71) Applicant: Ossur Iceland ehf, Reykjavik (IS)

(72) Inventor: Geoffrey Brown, Chelmsford (GB)

(73) Assignee: Ossur Iceland ehf, Reykjavik (IS)

(*) Notice: Subject to any disclaimer, the term of this patent is extended or adjusted under 35 U.S.C. 154(b) by 0 days.

(21) Appl. No.: 14/770,273

(22) PCT Filed: Feb. 6, 2014

(86) PCT No.: PCT/GB2014/050339
§ 371 (c)(1),
(2) Date: Aug. 25, 2015

(87) PCT Pub. No.: WO2014/132029
PCT Pub. Date: Sep. 4, 2014

(65) Prior Publication Data
US 2016/0000584 A1    Jan. 7, 2016

(30) Foreign Application Priority Data
Feb. 26, 2013    (GB) .................................... 1303341

(51) Int. Cl.
*A61F 2/78*    (2006.01)
*E05B 15/00*    (2006.01)
*A61F 2/80*    (2006.01)
*A61F 2/50*    (2006.01)

(52) U.S. Cl.
CPC .................. *A61F 2/78* (2013.01); *A61F 2/80* (2013.01); *A61F 2002/502* (2013.01); *A61F 2002/785* (2013.01); *A61F 2002/7875* (2013.01); *A61F 2220/0041* (2013.01); *E05B 15/00* (2013.01); *E05B 15/0006* (2013.01); *E05B 15/008* (2013.01); *E05B 15/0013* (2013.01);
(Continued)

(58) Field of Classification Search
CPC ................. A61F 2220/0041; A61F 2002/7875
See application file for complete search history.

(56) References Cited

U.S. PATENT DOCUMENTS

| 980,457 A | 1/1911 | Toles |
| 1,398,824 A | 11/1921 | Abrams |
| 1,893,853 A | 1/1933 | Tullis |

(Continued)

FOREIGN PATENT DOCUMENTS

| DE | 745 981 C | 5/1944 |
| DE | 813 190 C | 7/1949 |

(Continued)

OTHER PUBLICATIONS

English translation of Chinese Office Action, Chinese Patent Application No. 201480010447.5 dated Mar. 3, 2016.
(Continued)

*Primary Examiner* — Jacqueline Woznicki
(74) *Attorney, Agent, or Firm* — Workman Nydegger

(57) ABSTRACT

An attachment lock (27) for a prosthetic limb including a housing (28) having an opening (32) for insertion of a prosthetic locking pin (13). A locking member (29) is mounted within the housing (28) and is arranged releasably to secure an inserted locking pin (13). The lock (27) includes means (35) to adjust the position of the locking member (29) relative to the housing (28) along the axis of an inserted locking pin (13).

9 Claims, 3 Drawing Sheets

(52) U.S. Cl.
CPC ....... *E05B 15/0046* (2013.01); *E05B 15/0053* (2013.01); *E05B 2015/0066* (2013.01)

(56) References Cited

U.S. PATENT DOCUMENTS

| | | | |
|---|---|---|---|
| 2,530,285 A | 11/1950 | Catranis | |
| 2,533,404 A | 12/1950 | Sharp et al. | |
| 2,634,424 A | 4/1953 | Gorman | |
| 2,671,225 A | 3/1954 | Schoene et al. | |
| 2,808,593 A | 10/1957 | Andersen | |
| 3,393,407 A | 7/1968 | Kandel | |
| 3,671,980 A | 6/1972 | Baird | |
| 4,564,365 A | 1/1986 | Winer et al. | |
| 4,923,474 A | 5/1990 | Klasson et al. | |
| 4,938,775 A * | 7/1990 | Morgan | A61F 2/60 623/27 |
| 5,007,937 A | 4/1991 | Fishman et al. | |
| 5,139,523 A | 8/1992 | Paton et al. | |
| 5,163,965 A | 11/1992 | Rasmusson et al. | |
| 5,226,918 A | 7/1993 | Silagy et al. | |
| 5,314,496 A | 5/1994 | Harris et al. | |
| 5,376,129 A | 12/1994 | Faulkner et al. | |
| 5,376,131 A | 12/1994 | Lenze et al. | |
| 5,413,392 A * | 5/1995 | Schlack | E05B 9/00 292/204 |
| 5,507,837 A * | 4/1996 | Laghi | A61F 2/76 264/274 |
| 5,549,709 A | 8/1996 | Caspers | |
| 5,593,454 A | 1/1997 | Helmy | |
| 5,658,353 A | 8/1997 | Layton | |
| 5,662,715 A | 9/1997 | Slemker | |
| 5,702,489 A | 12/1997 | Slemker | |
| 5,718,925 A * | 2/1998 | Kristinsson | A61F 2/5046 264/573 |
| 5,728,170 A | 3/1998 | Becker et al. | |
| 5,735,906 A | 4/1998 | Caspers | |
| 5,882,053 A * | 3/1999 | Bekins | E05B 1/003 292/336.3 |
| 5,888,216 A | 3/1999 | Haberman | |
| 5,904,722 A | 5/1999 | Caspers | |
| 5,931,872 A | 8/1999 | Lohmann | |
| 5,972,036 A | 10/1999 | Kirstinsson et al. | |
| 6,063,125 A | 5/2000 | Arbogast et al. | |
| 6,106,559 A | 8/2000 | Meyer | |
| 6,123,340 A | 9/2000 | Sprafka et al. | |
| 6,149,691 A | 11/2000 | Fay et al. | |
| 6,231,616 B1 | 5/2001 | Helmy | |
| 6,231,617 B1 | 5/2001 | Fay | |
| 6,273,918 B1 | 8/2001 | Yuhasz et al. | |
| 6,287,345 B1 | 9/2001 | Slemker et al. | |
| 6,361,568 B1 | 3/2002 | Hoerner | |
| 6,402,789 B1 | 6/2002 | Gramnas | |
| 6,440,173 B1 | 8/2002 | Meyer | |
| 6,508,842 B1 | 1/2003 | Caspers | |
| 6,554,868 B1 | 4/2003 | Caspers | |
| 6,585,774 B2 | 7/2003 | Dean, Jr. et al. | |
| 6,645,253 B2 | 11/2003 | Caspers | |
| 6,726,726 B2 | 4/2004 | Caspers | |
| 6,761,742 B2 | 7/2004 | Caspers | |
| 7,056,303 B2 | 6/2006 | Dennis et al. | |
| 7,234,108 B1 | 6/2007 | Carstens | |
| 7,351,367 B2 | 4/2008 | Swanson, Sr. | |
| 7,427,297 B2 | 9/2008 | Patterson et al. | |
| 7,637,958 B2 | 12/2009 | Coop | |
| 7,771,487 B2 | 8/2010 | Mantelmacher | |
| 8,211,187 B2 | 7/2012 | Slemker et al. | |
| 2001/0005798 A1 | 6/2001 | Caspers | |
| 2001/0016781 A1 | 8/2001 | Caspers | |
| 2002/0040248 A1 | 4/2002 | Karason | |
| 2002/0087215 A1 | 7/2002 | Caspers | |
| 2002/0091449 A1 | 7/2002 | Caspers et al. | |
| 2002/0099450 A1 | 7/2002 | Dean, Jr. et al. | |
| 2003/0191539 A1 | 10/2003 | Caspers | |
| 2004/0030411 A1 | 2/2004 | Caspers | |
| 2004/0098136 A1 | 5/2004 | Caspers | |
| 2004/0122528 A1 | 6/2004 | Egilsson | |
| 2004/0143345 A1 | 7/2004 | Caspers | |
| 2004/0167638 A1 | 8/2004 | Caspers | |
| 2004/0181290 A1 | 9/2004 | Caspers | |
| 2004/0236434 A1 | 11/2004 | Carstens | |
| 2004/0243251 A1 * | 12/2004 | Carstens | A61F 2/7812 623/34 |
| 2005/0244220 A1 | 11/2005 | Ingimarsson | |
| 2007/0055383 A1 * | 3/2007 | King | A61F 2/68 623/34 |
| 2011/0307080 A1 | 12/2011 | Perkins et al. | |
| 2012/0310371 A1 | 12/2012 | Bachus et al. | |
| 2013/0195540 A1 | 8/2013 | Wozencroft et al. | |

FOREIGN PATENT DOCUMENTS

| | | |
|---|---|---|
| DE | 1 795 809 U | 9/1959 |
| DE | 2 060 239 A1 | 6/1972 |
| DE | 25 40 138 A1 | 3/1977 |
| DE | 2729800 | 1/1979 |
| DE | 32 21 920 A1 | 4/1983 |
| DE | 35 08 919 A1 | 9/1986 |
| DE | 94 19 208.1 U1 | 11/1994 |
| GB | 267 988 | 9/1925 |
| GB | 2 069 847 A | 9/1981 |
| GB | 2 087 727 A | 6/1982 |
| GB | 2338899 A | 1/2000 |
| JP | 07-155343 A | 6/1995 |
| WO | 00/74611 A2 | 12/2000 |
| WO | 01/54631 A1 | 8/2001 |
| WO | 03/024367 A2 | 3/2003 |
| WO | 03/024370 A1 | 3/2003 |
| WO | 03/039398 A1 | 3/2003 |
| WO | 03/099173 A1 | 12/2003 |

OTHER PUBLICATIONS

2nd Office Action (and English Translation) of Chinese Patent Application No. 201480010447.5, dated Aug. 26, 2016.

* cited by examiner

PROSTHETIC ATTACHMENT LOCK

The present application is a 371 of International application PCT/GB2014/050339, filed Feb. 6, 2014, which claims priority of GB 1 303 341.0, filed Feb. 26, 2013, the priority of these applications is hereby claimed and these applications are incorporated herein by reference.

BACKGROUND OF THE INVENTION

This invention relates to an attachment lock for a prosthetic limb.

A prosthetic socket is used in the connection of a residual limb to a prosthetic limb and is formed from a sufficiently rigid material which possesses the required load bearing capacity. Typically, a liner is positioned between the residual limb and the socket. The liner is usually a flexible material which is rolled onto the residual limb. Various types of liner are available and these may serve merely to protect the skin of the residual limb and also to provide comfort to the wearer. Some liners, known as locking liners, are configured with a locking pin which connects to an attachment lock. The attachment lock serves to connect a socket to the liner.

There are many different types of attachment lock available. The most commonly used locks are either ratchet-type locks or clutch-type locks. There are also various types of locking pin, the most appropriate type chosen depending on the type of lock used. Rastered locking pins are typically used for ratchet type locks and these have sloped (saw-tooth) serrations along the shaft. When a rastered pin is inserted into a ratchet-style lock, the serrations urge the locking member to one side. Once a serration has moved past the locking member, the locking member moves back to the original position. The rastered pin has a flat edge which prevents the rastered pin from being pulled out of the lock. This invention had been developed primarily for use with ratchet-style locks and rastered locking pins, though it will be appreciated that it is not limited to such use.

Most prosthetic sockets are fabricated with the attachment lock moulded therein. A mounting coupling is used to connect the attachment lock to a prosthetic limb. The attachment lock and mounting coupling are available as either a single unit or as separate distinct components. A single lock and coupling unit is generally used with glass reinforced laminated sockets, where the unit is laminated into the cloth and fibre layers making up the distal end of the socket, in order to attain enough weight bearing capacity. Where a thermoplastic socket is required, a separate lock and coupling is usually used, with the coupling being integrated into an additional 'outer' socket. In order to gain access to the attachment lock and/or the mounting coupling in each of these cases the socket must be cut.

An important factor which must be taken into account is the orientation of the prosthetic limb with the prosthetic socket. This is particularly pertinent on trans-femoral sockets where the orientation of the prosthetic limb relative to the socket must be determined to optimise the knee axis. With these existing sockets the optimum orientation is difficult to achieve because the attachment lock is formed into the socket during manufacture. The orientation must therefore be selected before fitting evaluation is performed and thus is not tailored towards a specific patient.

To ensure a safe and comfortable connection, prosthetic sockets must be custom-made so as to compliment the shape of the residual limb. Sockets are available in a range of different materials and are formed using different methods. This inevitably results in sockets with variations in thickness. A properly fitted prosthetic limb, with a locking pin arrangement, requires the locking pin to be fully inserted into the lock. It is not uncommon, with rastered pins and ratchet-type locks, for this full insertion to result in free play of the lock between two serrations. A small amount of free play is acceptable, but too much can cause significant problems. Firstly, this free play gives a slack connection, such that the residual limb may move up and down within the socket when the patient is walking (known as pistoning). Secondly, it can create an undesirable noise, which can be of great annoyance and embarrassment to the patient. Thirdly, the free play can lead to premature wear of the pin and lock components which can ultimately result in failure of the lock.

SUMMARY OF THE INVENTION

It is a principal aim of the present invention to provide an attachment lock which addresses at least some of the above problems.

According to this invention, there is provided an attachment lock for a prosthetic limb comprising:
- a housing having an opening for insertion of a prosthetic locking pin;
- a locking member mounted within the housing and arranged releasably to secure an inserted locking pin; and
- means to adjust the position of the locking member relative to the housing along the axis of an inserted locking pin.

The locking member may contain a ratchet-type lock and the invention will be described with particular emphasis on this type of lock, though it will be appreciated that other types of suitable lock may also be used.

The arrangement of the attachment lock is such that it facilitates axial adjustment of the position at which an inserted locking pin may be held. In this way fine adjustments may be made to allow the amount of free play between the locking member and two serrations of the locking pin to be optimised.

The invention is particularly suitable for use during prosthetic socket fit evaluation, though it will be appreciated that it is not limited to such use and may be incorporated into definitive sockets for long term use.

The prosthetic locking pin may be provided at the distal end of a prosthetic liner. The attachment lock serves to connect the residual limb, indirectly or directly, to a prosthetic socket. Preferably, the housing includes a mounting member configured releasably to mount the attachment lock to the prosthetic socket such that a locking pin may be inserted in the opening. The mounting member is also suitably configured for attachment, either releasably or permanently, to a prosthetic limb. As such, the alignment of the attachment lock relative to the prosthetic socket is important to ensure that the prosthetic limb is appropriately positioned on the patient.

There are various ways the mounting means can be configured to connect the attachment lock to a socket. Preferably, the socket has a hole formed in the distal end for the insertion of a locking pin and the mounting means is configured for mounting to the socket so that the hole of the socket is in register with the opening of the housing. At least two holes may be formed through the mounting member, with each hole being configured for attaching the mounting member to a prosthetic socket. More than two holes may of course be provided and it is most likely that four holes will be used. Corresponding holes are formed in the socket and the attachment lock may be mounted to the socket by securing the mounting member using suitable fixings such as nuts and bolts. An advantage of this arrangement is that the mounting holes in the socket are not pre-formed but instead may be drilled during fitting of the prosthetic limb. In this way, the optimum orientation of the attachment lock on the socket may be selected by rotation of the attachment lock before the holes are formed in the socket. This is particularly useful for many trans-femoral sockets, where the orientation of the prosthetic limb relative to the socket must be determined to optimise the knee axis, and where the connection adaptor used to connect the prosthetic limb to the attachment lock does not have the facility to rotate. Preferably a clamping member is located within the socket, at the distal end thereof, to provide a structure for securing the mounting fixings of the attachment lock. A flexible sealing ring may also be provided on the clamping member to support the distal end of an inserted liner. The sealing ring is preferably formed from a visco-elastic type material such that it conforms to the shape of the patient's liner.

Preferably, the means to adjust the position of the locking member relative to the housing comprises a spacer of a selected thickness positioned between the locking member and the housing. In this way the spacer with the most appropriate thickness may be selected to ensure the optimum amount of free play of the lock member between two serrations. Additionally, or alternatively the means may comprise a plurality of spacers of the same or different thickness. The, or each spacer may be positioned above and/or below the locking member depending on whether the locking member is to be lowered or raised. So as to enhance stability and ensure a uniform amount of free play of the locking member relative to the locking pin, it is advantageous if the spacer has a hole in register with the opening.

The attachment lock preferably includes a release member operatively connected to the locking member and operable to release the locking member from an inserted locking pin. The release member enables the disconnection of the locking pin from the attachment lock and allows the patient to remove the attachment lock in a quick and easy manner. Where the attachment lock is connected to a socket and to a prosthetic limb, by simple operation of the release member, the patient may detach the prosthetic limb in a quick and easy manner. To reattach the prosthetic limb, the patient simply inserts the locking pin into the attachment lock so that it engages with the locking member.

In a preferred arrangement, the release member comprises a rod releasably connected to the locking member. In this way, the rod may be screw threaded and the locking member configured so that the rod is engageable therewith. Sometimes, a prosthetic socket is covered with a cosmetic foam and the arrangement of a releasable locking member allows the length of the rod to be selected (by cutting or otherwise) in order to suit the depth of the cosmetic foam. Where cosmetic foam is not used the rod can be cut short to allow the rod to fit snugly shielded under the socket.

The rod may be pushed into the attachment lock so as to urge the locking member to one side and thus allow upward axial movement of the locking pin within the attachment lock. A button or knob is preferably provided on the rod to assist operation thereof. The direct coupling of the locking member with the rod ensures that the locking member may be released, if it were to get lodged in a locking position, by simply tapping the button firmly. Conversely, should the locking member lodge in an open position the locking member may be reengaged by pulling the rod away from the attachment member.

It is not uncommon for damage to prosthetic attachment locks to occur as a result of foreign material entering the locking member. The locking member of the present invention preferably has a closed design so that ingress of dirt or debris into the locking mechanism is prevented.

The attachment lock of this invention addresses the problems associated with variations in the thickness of the distal end of a prosthetic socket. The attachment lock may be removed easily without damage to a socket and can be repaired or replaced. This is particularly beneficial during prosthetic socket fit evaluations where the most appropriate selection of parts may be tailored specifically to the patient without non-suitable parts being damaged. The invention is also applicable to use with definitive sockets and indeed with sockets formed from different materials, including thermoplastic sockets and glass reinforced sockets. The orientation of the prosthetic limb relative to the socket may also be tailored specifically to the patient.

By way of example only, one specific embodiment of attachment lock of this invention will now be described in detail, reference being made to the accompanying drawings in which:

DETAILED DESCRIPTION OF THE INVENTION

Figures 1, 2:
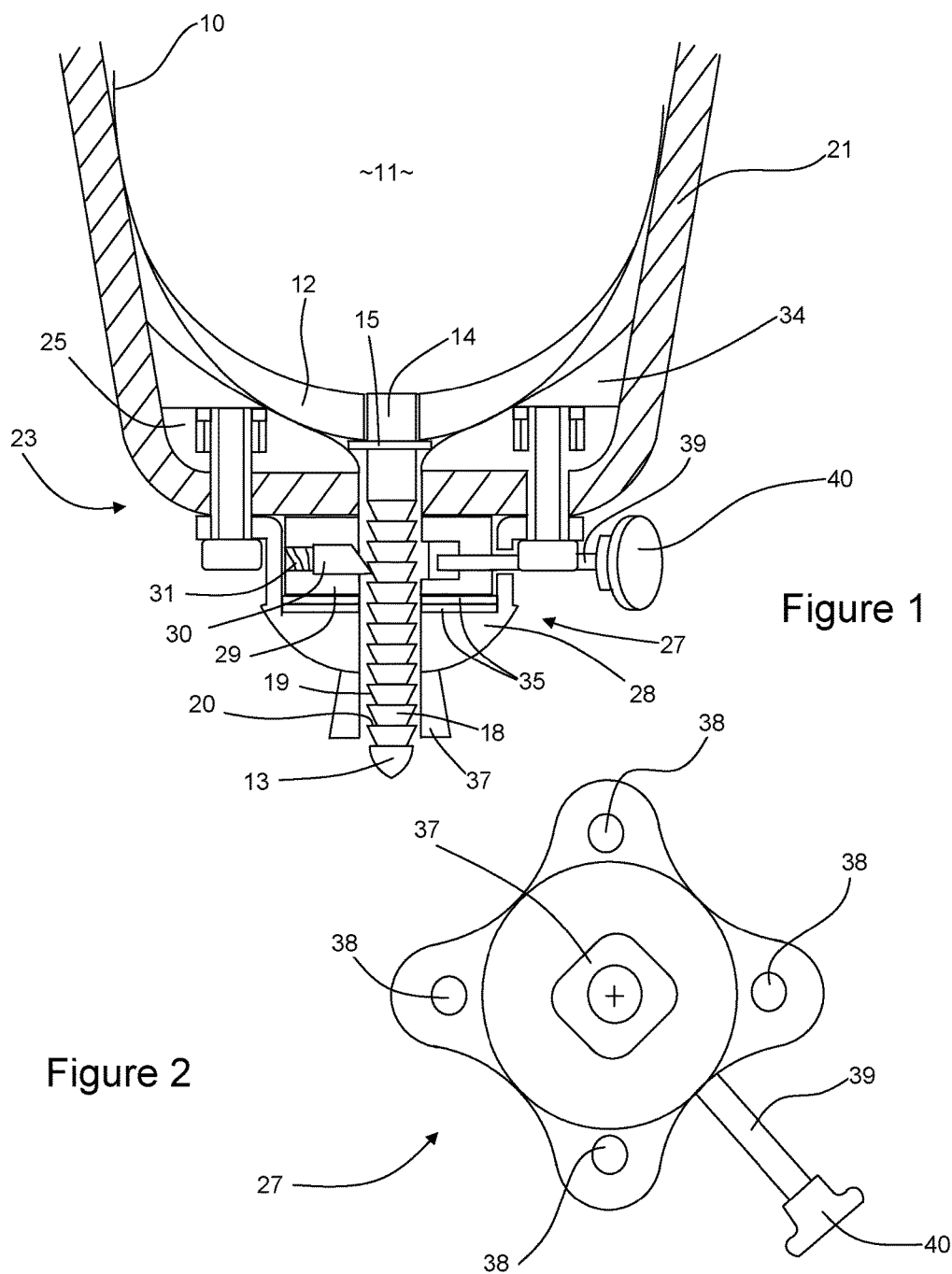
FIG. 1 is a cross-sectional front view of the attachment lock of the present invention connected to a socket.
FIG. 2 is a view of the underside of the attachment lock.
Figure 3:
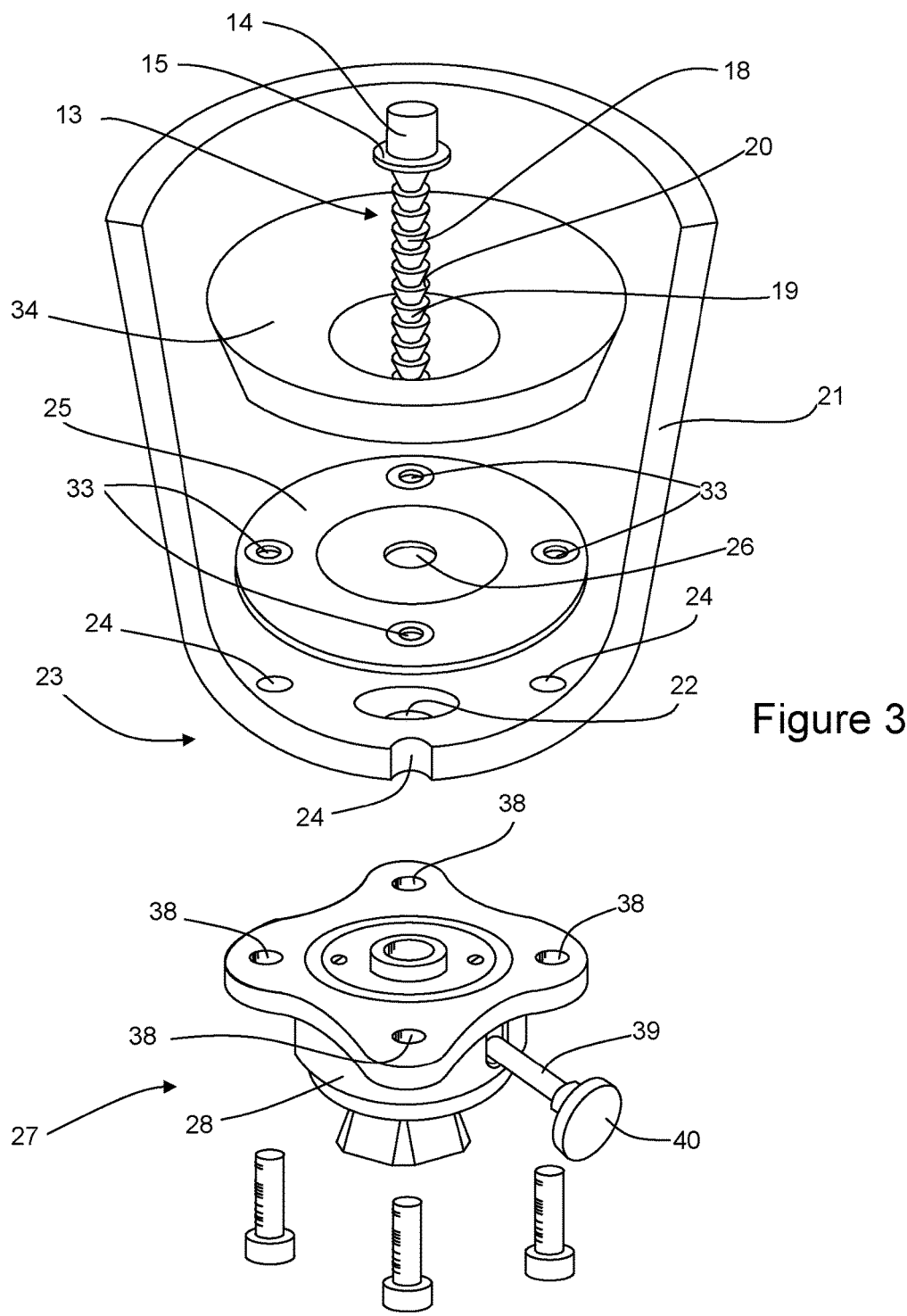
FIG. 3 is a cross-sectional exploded view of the attachment lock connected to a socket.
Figure 4:
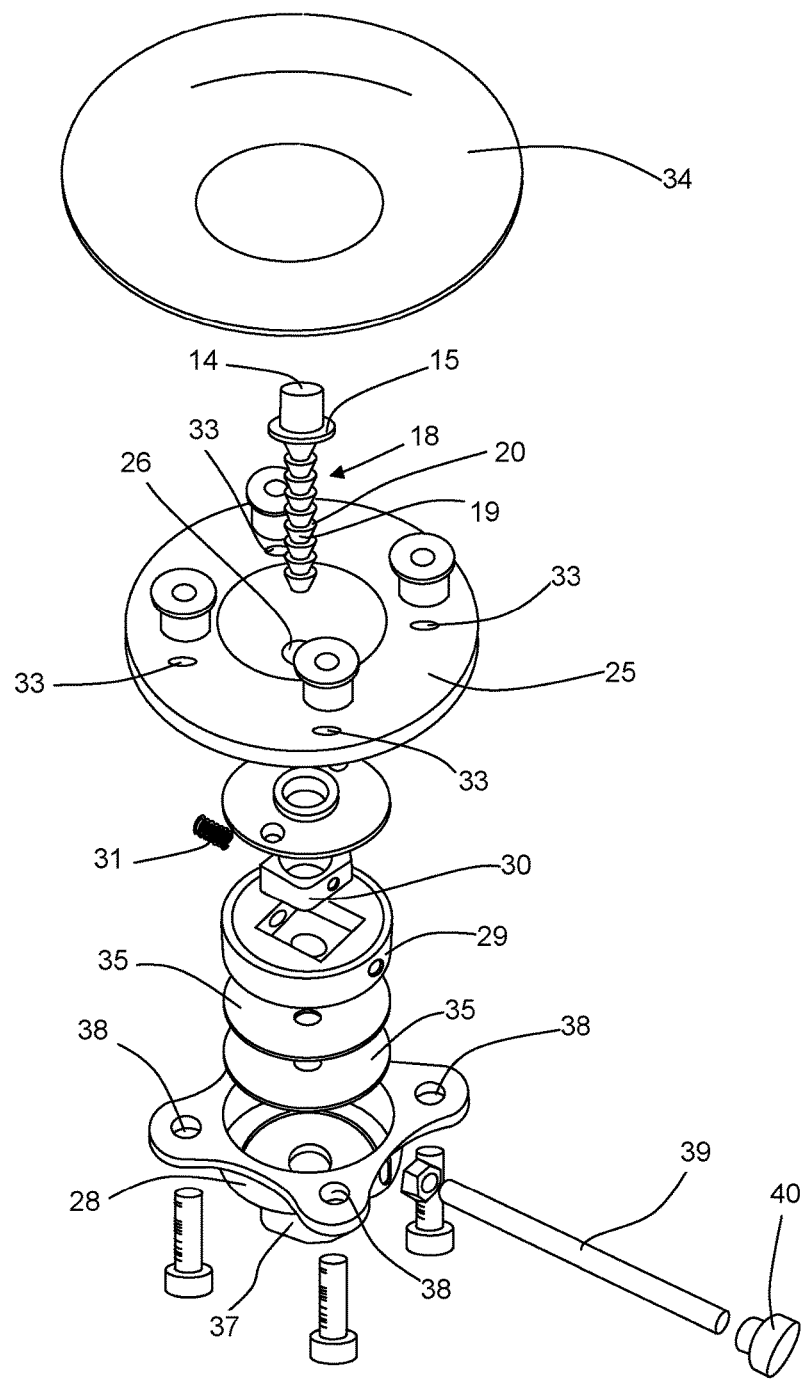
FIG. 4 is an exploded view of the attachment lock.

Referring initially to FIG. 1 there is shown a prosthetic liner 10 connected to the residual limb 11 of a patient (not shown). The liner 10 has a reinforced distal end 12 configured for connection of a prosthetic locking pin 13. The locking pin 13 is a rastered locking pin having a connecter 14, which is screwed into a threaded bush in the liner 10 and adhered thereto for added security. A shoulder 15 separates the connector 14 from sloped (saw-tooth) serrations 18 along the length of the shaft. Each serration 18 is defined by a sloped part 19 and a flat edge 20.

FIGS. 1 and 2 show a trans-femoral prosthetic socket 21 which is formed from a rigid material and is custom-made to correspond to the shape and configuration of the patients residual limb 11. The socket 21 has an opening 22 formed in the distal end 23 for receiving the locking pin 13. Mounting holes 24 are also formed through the distal end 23 of the socket 21. An annular clamping plate 25 having an opening 26 formed therethrough is located within the socket and has holes 33 in registration with the mounting holes 24. A flexible sealing ring 34 is positioned above the clamping plate. The sealing ring is formed from a foam-like material and is arranged to conform to the shape of the liner 10 so as to provide support to the residual limb 11.

Referring now to all of the Figures, an attachment lock 27 connects the socket 21 to the liner 10 and comprises a housing 28 in which a locking member 29 is contained. The locking member 29 contains a ratchet-type lock having a pawl member 30 connected to a spring 31 and configured to engage the serrations 18 of the locking pin 13. An opening 32 is formed in the attachment lock 27, which allows the locking pin 13 of a liner 10 to be inserted into the attachment lock and to engage with the pawl member 30 of the locking member 29. A release member is provided to disengage the pawl member 30 from the serrations 18 of the locking pin 13 and this comprises a rod 39 releasably connected to the pawl member 30 and having a manually operable button 40 at one end.

The attachment lock 27 includes means to adjust the position of the locking member relative to the housing along the axis of an inserted locking pin and in the figures the means comprises two spacers 35. The spacers 35 are positioned between the locking member 29 and the housing 28 in order to reduce the amount of free play between the pawl 30 and the two adjacent serrations 18. This serves to prevent the occurrence of pistoning and undesirable noise. In this arrangement the spacers have openings 36 in registration with the opening 32 formed in the attachment lock 27 and are provided below the locking member 29 so as to raise the member 29 relative to the housing 28.

A pyramid-shaped adaptor 37 is provided at the distal end of the housing 28 and is used to connect a prosthetic limb (not shown) to the attachment lock 27. The housing 28 includes mounting holes 38 for mounting the attachment lock 27 to the socket 21. In a preferred arrangement, the mounting holes 24 in the socket 21 are not pre-formed but are drilled during fitting of the socket 21 so that the orientation of the attachment lock 27 relative to the socket can be tailored specifically to the patient.

The invention claimed is:

1. An attachment lock for a prosthetic limb comprising:
    a housing attachable to an outer surface of a prosthetic socket, and defining a distal end having an adaptor for connecting the housing to the prosthetic limb;
    a locking member contained within the housing, the locking member carrying a pawl member and a rod connected to the pawl member;
    an opening extending through the housing and the locking member, the opening arranged to allow a locking pin of a liner to be inserted into the attachment lock and to engage with the pawl when the locking pin is inserted into the attachment lock; and
    at least one spacer selectively positionable in the housing in different arrangements below and above the locking member so as to reduce free play between the pawl member and two adjacent serrations on the locking pin by raising and lowering the locking member including the pawl member and the rod relative to the housing along a longitudinal axis of the locking pin, wherein the at least one spacer defines a central opening arranged to allow the locking pin to extend through the at least one spacer.

2. The attachment lock of claim 1, wherein the housing includes a mounting member configured to releasably mount the housing to the outer surface of the prosthetic socket.

3. The attachment lock of claim 2, wherein at least two holes are formed through the mounting member, each hole being configured for attaching the mounting member to the prosthetic socket.

4. The attachment lock of claim 1, wherein the housing is arranged so that the locking pin protrudes distally beyond the housing.

5. The attachment lock of claim 1, further comprising a release member operatively connected to the locking member and arranged to selectively release the pawl member from the locking pin.

6. The attachment lock of claim 5, wherein the release member moves the locking member in a transverse direction relative to a length of the opening of the attachment lock and the at least one spacer moves the locking member in a vertical direction relative to a bottom of the housing.

7. The attachment lock of claim 1, wherein the locking member include a ratchet-type lock.

8. The attachment lock of claim 1, further comprising a spring connected to the pawl member.

9. The attachment lock of claim 1, wherein the at least one spacer comprises a plurality of spacers.

* * * * *